United States Patent [19]

Lechner et al.

[11] Patent Number: 4,946,901

[45] Date of Patent: Aug. 7, 1990

[54] POLYMERIZABLE COMPOSITIONS, PROCESS FOR THE PREPARATION THEREOF, AND USE THEREOF AS DENTAL COMPOSITIONS

[75] Inventors: Günther Lechner, Frieding; Klaus Ellrich, Wörthsee; Rainer Guggenberger; Oswald Gasser, both of Seefeld, all of Fed. Rep. of Germany

[73] Assignee: ESPE Stiftung & Co. Produktions- und Vertriebs KG, Seefeld, Fed. Rep. of Germany

[21] Appl. No.: 348,078

[22] Filed: May 4, 1989

Related U.S. Application Data

[63] Continuation of Ser. No. 130,080, Dec. 8, 1987, abandoned.

[30] Foreign Application Priority Data

Dec. 10, 1986 [DE] Fed. Rep. of Germany ....... 3642212

[51] Int. Cl.$^5$ ........................ C08F 265/06; A61K 6/08
[52] U.S. Cl. ..................................... 525/305; 525/279;
525/289; 525/303; 525/304; 525/309; 522/120;
522/121; 523/115; 523/116; 523/117
[58] Field of Search ....................... 525/304, 305, 309;
523/115, 116, 117; 522/120, 121

[56] References Cited

U.S. PATENT DOCUMENTS

| | | | |
|---|---|---|---|
| 3,914,341 | 10/1975 | Kliment | 525/305 |
| 4,369,262 | 1/1983 | Walkowiak | 525/309 |
| 4,394,465 | 7/1983 | Podszun | 525/305 |
| 4,437,836 | 3/1984 | Schmitz-Josten | 522/27 |
| 4,521,505 | 6/1985 | Podszun | 430/112 |
| 4,603,726 | 8/1986 | Pfannenstiel | 164/35 |

OTHER PUBLICATIONS

Wojcik, Porous Bead Aliphatic-Aromatic Methacrylate Copolymers II, Angew. Makromol. Chem. 121, p. 89; 1984.
Wojcik, Porous Bead Aliphatic-Aromatic Methacrylate Copolymers I, Angew. Makromol. Chem. 119 p. 193; 1983.
Almog, Monodisperse Polymeric Spheres in the Micron Size, Brit. Polym. J. 14, p. 131; 1982.
"Skinner's Science of Dental Materials" pp. 177-193; 1982.
Barrett, Dispersion Polymerization in Organic Media, Brit. Polym. J. 5 pp. 259-271; 1973.

*Primary Examiner*—John C. Bleutge
*Assistant Examiner*—David Buttner
*Attorney, Agent, or Firm*—Robert W. Becker & Associates

[57] ABSTRACT

Polymerizable compositions are described on the basis of (meth)acrylic acid esters which contain as filler a precipitation polymer that is formed from acrylic acid esters and/or methacrylic acid esters, and possibly other copolymerizable monomers, with 10 to 100 mol % of the (meth)acrylic acid esters being bi or polyfunctional. These compositions are particularly suitable as dental compositions.

14 Claims, No Drawings

POLYMERIZABLE COMPOSITIONS, PROCESS FOR THE PREPARATION THEREOF, AND USE THEREOF AS DENTAL COMPOSITIONS

This application is a continuation of application Ser. No. 130,080 filed Dec. 8, 1987.

BACKGROUND OF THE INVENTION

The present invention relates to polymerizable compositions, a process for the preparation thereof, and the use of said compositions as dental compositions.

It has been known for a long time to make up dental compositions, such as, for example, tooth filling materials, veneer and crown materials, orthodontic base materials, etc., from polymerizable ethylenically unsaturated monomers (usually mono or polyfunctional methacrylic esters), and to mix the latter with fillers to give them essential desired properties. These include obtaining a pasty consistency, adjustment of optical and cosmetic effects, reduction of the polymerization shrinkage, and, if reinforcing fillers are used, improving the mechanical properties such as compressive and flexural strength, and surface hardness, etc.

Apart from inorganic fillers, such as quartz or glasses in finely ground form or dispersive silicic acids, organic fillers are also used. Organic fillers are particularly appropriate when specific processing properties or specific optical effects (e.g. high transparency) or complete combustibility of the material are of significance. As apparent for example from "Skinner's Science of Dental Materials", W. B. Saunders Company 1982, p. 177 et seq., p. 245, bead-like polymers of methylmethacrylate (possibly with slight additions of bifunctional crosslinking monomers) having an average grain size of 20–30 $\mu$m are a widely used organic filler. These beads are mixed, for example, with methylmethacrylate and within a few minutes the mixture swells to give a doughy mass which mixed with the usual polymerization initiators, can be formed in suitable hollow molds and subsequently polymerized. However, because of the swelling behavior it is not possible to make monocomponent materials on this basis. Said systems are used inter alia for denture plastics, veneer and crown materials, modelling plastics, and tooth filling materials.

German reference No. 2,850,916 Walkowiak et al. dated June. 12, 1980 corresponding to U.S. Pat. No. 4,369,262-Walkowiak et al. dated Jan. 18, 1983, discloses highly crosslinked bead polymers which hardly swell after mixing with the monomers. However, due to the higher density compared with the monomer component, they have the tendency to sediment in the mixtures so that as a rule inorganic antisedimentation agents must be used to suppress this tendency. This has, however, decisive influence on the optical properties and the complete combustibility of these materials. Moreover, as a rule these polymers do not have a strengthening effect.

In Houben-Weyl, Volume XIV/1, p. 133 et seq., the preparation of voluminous powders by precipitation polymerization from acrylic acid esters is described. A. B. Wojcik specifically described such polymers in Angew, Makromol. Chem. 119, 193 (1983) and 121, 89 (1984). However, not even a hint is given anywhere as to the use of such polymers as fillers in dental materials. The fact that the use of such polymers as fillers in dental materials is not considered in this publication is apparent not least from Houben-Weyl, loc. cit., p. 146 where the following is stated: "Lumpy precipitation or coagulation is a frequently encountered unfortunate secondary effect which must be overcome by variation of the solubility conditions."

One object of the present invention is to provide an organic filler for compositions, in particular dental materials, containing (meth)acrylic esters which exhibits practically no swelling behavior, has a strengthening effect, and permits the preparation of stable non-sedimenting monocomponent preparations. Another object is to retain the optical, mechanical, and toxicological properties essential to dental materials.

These and other objects and advantages of the present invention will appear more clearly from the following specification in conjunction with the accompanying Examples.

SUMMARY OF THE INVENTION

The present invention provides polymerizable compositions containing as filler a precipitation polymer formed from acrylic acid esters and/or methacrylic acid esters and possibly other copolymerizable monomers, with 10 to 100 mol % of the (meth)acrylic acid esters being bi or polyfunctional.

It has been found according to the invention that such precipitation polymers can be used as strengthening fillers in dental materials on the basis of mono, bi or polyfunctional (meth)acrylic acid esters. These fillers enable monocomponent preparations to be made because they exhibit neither swelling nor sedimentation behavior. In addition, they enable compositions to be made which are combustible without leaving any residue.

The precipitation polymers comprise, as mentioned above, acrylic acid esters and/or methacrylic acid esters: addition of other copolymerizing monomers is possible provided that the properties of the precipitation polymers are not negatively influenced. Examples of such comonomers are styrene, vinyl, ether, unsaturated carboxylic acids and the esters thereof, fumaric acid esters, maleic acid esters, acrylonitrile, and the like. At least 10 mol % of the (meth)acrylic acid esters must be bi or polyfunctional; it is advantageous for the proportion of said esters to be at least 20 mol %, preferably at least 60 mol %, and particularly suitable precipitation polymers are formed 100% from bi or polyfunctional (meth)acrylic acid esters.

Suitable bifunotional (meth)acrylic acid esters are bis-GMA (reaction product of bisphenol A with 2 mole equivalent glycidyl methacrylate), triethyleneglycol dimethacrylate, ethyleneglycol dimethacrylate, and the (meth)acrylic acid esters named in German Pat. No. 1,921,869, Schmitt et al. dated Mar. 2, 1972 German Pat. No. 2,816,823, Schmitt et al. dated Apr. 29, 1982 and German reference No. 3,607,331 Schmitt et al. dated Sept. 10, 1987. The U.S. counterparts for these three German patent disclosures are U.S. Pat. Nos. 3,923,740-Schmitt et al. dated Dec. 2, 1975; 4,131,729-Schmitt et al. dated Dec. 26, 1978; and 4,795,823-Schmitt et al. dated Jan. 3, 1989, respectively, all belonging to the assignee of the present invention.

The precipitation polymers according to the invention consist of essentially irregular agglomerate particles (secondary particles) having a grain size of about 0.2 to 200 $\mu$m. The weight average of the grain distribution of the secondary aggregates lies between 5 $\mu$m and 100 $\mu$m. and precipitation polymers are preferred with a weight average of the grain size between 10 $\mu$m and 50 μm. To a small extent non-agglomerated primary particles may also be present.

The agglomerates are formed from primary particles whose grain size lies between 0.05 μm and 2 μm. Preferred are precipitation polymers whose primary particles have a grain size between 0.1 μm and 1 μm.

The grain size of the secondary particles can be determined, for example, by screen analysis or in particularly advantageous manner by laser granulometry. The size of the primary particles is obtained from the measurement of images formed by raster electronmicroscope; it is convenient to measure particles which are located at the periphery of the agglomerates and fused to the agglomerate only to such an extent that their diameter is still apparent.

A further characteristic of the precipitation polymers according to the invention is their BET surface area; this lies in the range between 5 and 300 m²/g; preferred are polymers having a surface area between 10 and 200 m²/g, and polymers having a surface area between 50 and 100 m²/g are particularly suitable.

DESCRIPTION OF PREFERRED EMBODIMENTS

Hereinafter the preparation on of the precipitation polymers will be described in detail.

Advantageously, the precipitation polymers are prepared analogously to the process of dispersion polymerization. The preparation is described by K. E. J. Barrett, Brit. Polym. J. 5, 259–271 (1973) and K. Almog et al.. Brit. Polym. J. 14 131 (1982), and in the following preparation examples.

Although the procedure adopted is that of dispersion polymerization, in fact precipitation polymerization takes place because the resulting polymers, due to their high proportion of bi and polyfunctional (meth)acrylic acid esters, are so sparely soluble that they cannot be kept in suspension even by the added dispersion stabilizer. Thus, on accumulating together, the precipitating polymer particles do not form beads, as in dispersion polymerization, but porous agglomerates consisting of spherical primary and irregular secondary particles.

Fundamentally, the preparation of the polymers according to the invention is also possible by the processes of precipitation polymerization, as described for example in Houben-Weyl, Volume XIV/1.

Hereinafter the use of the precipitation polymers will be explained in detail.

The precipitation polymers are used as strengthening fillers in dental materials on the basis of (meth)acrylic acid esters, exhibiting little tendency to ward swelling and sedimentation. The precipitation polymers are used in amounts by weight of 2 to 60% by weight, preferably 5 to 40% by weight, and particularly preferably 5 to 25% by weight, in each case with respect to the total composition. They may be used together with other inorganic and organic fillers.

Suitable monomers for the dental materials according to the invention are mono, bi or polyfunctional (meth)acrylic acid esters. Particularly suitable bifunctional (meth)acrylic acid esters are bis-GMA, triethyleneglycol dimethacrylate, and the (meth)acrylic acid esters named in German Patent 1,921,869, German Patent 2,816,823, and German reference 3,607,331.

The (meth)acrylic acid esters of German reference 3,607,331 are products of the general formula:

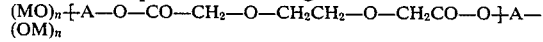

wherein:
A is an alcohol radical having at least 4 chain atoms between two linkage points,
M is $CH_2=C(R^1)-CO-$,
$R^1$ being hydrogen or methyl,
n is 1 or 2,
x is 0.3 or 3.

Apart from the precipitation polymers according to the invention and the monomers, the dental materials according to the invention may contain the polymerization initiators known to the expert.

By addition of peroxides, such as benzoyl peroxide or lauroyl peroxide, AIBN or other thermal radical formers, compositions are formed which can be cured by methods known in dental technology at elevated temperature, possibly under pressure.

For cold curing it is possible to use, for example, the initiator systems peroxide/amine, hydroperoxide/thiourea derivative, barbituric acid/peroxide/$Cu^{2+}$ ions/$Cl^-$ ions. The initiator components are distributed among different components of the dental composition according to the invention.

The precipitation polymers according to the invention are particularly suitable for the preparation of photopolymerizable dental compositions consisting of only one component. 0.1 to 10% by weight photoinitiators, with respect to the monomer component, is added to the compositions. The polymerization initiation is either with UV light or preferably with visible light in the wavelength range of 400–550 nm. Suitable photoinitiators are benzophenone, benzilketals, benzoin ether and, in particular for polymerization with visible light, aromatic or aliphatic diketones such as benzil, phenanthrenequinone or campherquinone, and mono or bisacylphosphone oxides.

In addition, the compositions can contain the usual stabilizers, inhibitors, coloring agents, pigments, opacifying agents, and/or X-ray contrast agents.

The precipitation polymers according to the invention are used for preparing tooth filling compositions, denture materials, veneer and crown materials, modelling plastics, orthodontic materials, and similar uses. The use of the inventive precipitation polymers is particularly advantageous when residue-free combustion of the hardened material is necessary, for example with a modelling material. Such a use is described, for example, in German reference 3,240,907 Pfannenstiel et al. dated Nov. 5, 1982, corresponding to U.S. Pat. No. 4,603,726-Pfannenstiel et al. dated Aug. 5,1986 ad belonging to the assignee of the present invention. However, the inventive precipitation polymers can also be used with particular advantage to make materials of high transparency, for example orthodontic materials. The properties of such materials are apparent from the following examples.

Hereinafter the invention will be explained in detail with the aid of examples.

Example 1

Preparation of a precipitation polymer 18 g: methylmethacrylate
12 g: glycol dimethacrylate
0.3 g: azoisobutyric acid nitrile
7 g: polyvinylpyrrolidone
are dissolved in 400 ml methanol at room temperature.

The reaction mixture is stirred for 24 h at 60° C. The resulting precipitate is extracted and dried. The product has a BET surface area of 8.3 m$^2$/g and an average secondary particle size of 31.6 μm The grain size distribution of the secondary particles as determined by laser granulometry is indicated by Table I.

EXAMPLE 2

A. Preparation of a methacrylic acid ester mixture (according to Example 1 of German reference 3,607,331)

Triglycolic acid-bis [3(4)-methacryloxymethyl-8(9)-tricyclo [5.2.1.0$^{2,6}$] decylmethyl ester].

196 g (1.0 mol) bis-(hydroxymethyl)-tricyclo [-5 2.1.0$^{2,6}$]decane (T-diol), dissolved in 400 ml cyclohexane, are partially esterified with removal of 18 g water with 89 g (0.5 mol) triglycolic acid. As catalyst 7 g p-toluene-sulfonic acid is used. The remaining hydroxyl functions of the diol are esterified with 129 g (1.5 mol) freshly distilled methacrylic acid with addition of 80 mg picric acid, 200 mg methylene blue, and 35 mg BHT as polymerization inhibitors, a further 18 g water being separated. The crude ester mixture is diluted with a further 400 ml cyclohexane and 250 ml toluene, and is washed with 4×350 ml 2-n NaOH, 2×350 ml 0.5-n H$_2$SO$_4$, and with water. The ester solution is dried with sodium sulfate, aerated with oxygen of the air, and subsequently purified over aluminum oxide. After addition of 4-methoxyphenol for inhibition, by concentration in a high vacuum 258 g of an ester mixture is obtained which has the following average composition: 32% T-diol-bis-methacrylate 38% triglycolic acid-bis-T-methacrylate 30% bis-(methyacrylate) of

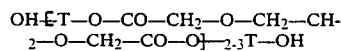

Viscosity: 80 poise
Density: 1.152 g/ml
$n_p^{20}$: 1,496

The methacrylic acid ester mixture corresponds to the above general formula given with reference German disclosure 3,607,331 with the following denotations:

A = bis-(hydroxymethyl)-tricyclo [5.2.1.0$^{2,6}$] decane
M = CH$_2$=C(CH$_3$)—CO—
n=1
x=1.3.

B. Preparation of the precipitation polymer

The preparation is carried out analogously to Example 1, but from:

15 g methacrylic acid ester mixture according to Section A
9 g polyglycol-400-dimethacrylate
6 g bishydroxymethyl-bicyclo 5.2.1.0$_{2,6}$] decanediacrylate
7 g polyvinylpyrrolidone
0.3 g azoisobutyric acid nitrile The dried product has a BET surface area of 15.9 m$^2$/g and an average secondary particle size of 34.3 μm.

The grain size distribution of the secondary particles determined by laser granulometry is given in Table I.

EXAMPLE 3

The preparation takes place analogously to Example 1, but from:

15 g glycol dimethyacrylate
15 g bishydroxymethyl-bicyclo [5 2.1.0$^{2,6}$] decanediacrylate
7 g polyvinylpyrrolidone
0.3 g azoisobutyric acid nitrile The dried product has a BET surface area of 72.3 m$^2$/g and an average secondary particle size of 16.2 μm.

The grain size distribution of the secondary particles determined by laser granulometry is given in Table I.

TABLE 1

| | Example 1 | | Example 2 | | Example 3 |
|---|---|---|---|---|---|
| μm | Distribution | μm | Distribution | μm | Distribution |
| 1 | 002,2% | 1 | 001,5% | 1 | 001,6% |
| 1,5 | 002,5% | 1,5 | 001,7% | 1,5 | 001,9% |
| 2 | 003,1% | 2 | 002,4% | 2 | 002,9% |
| 3 | 003,9% | 3 | 003,6% | 3 | 004,6% |
| 4 | 005,4% | 4 | 005,4% | 4 | 006,9% |
| 6 | 007,4% | 6 | 007,8% | 6 | 012,3% |
| 8 | 010,2% | 8 | 010,9% | 8 | 019,3% |
| 12 | 015,5% | 12 | 016,0% | 12 | 034,6% |
| 16 | 022,7% | 16 | 022,8% | 16 | 049,3% |
| 24 | 035,7% | 24 | 032,3% | 24 | 072,1% |
| 32 | 050,8% | 32 | 046,1% | 32 | 086,2% |
| 48 | 076,1% | 48 | 072,8% | 48 | 098,5% |
| 64 | 086,9% | 64 | 085,5% | 64 | 098,7% |
| 96 | 099,8% | 96 | 100,0% | 96 | 099,9% |
| 128 | 099,9% | 128 | 100,0% | 128 | 099,9% |
| 192 | 100,0% | 192 | 100,0% | 192 | 100,0% |
| 50% point = 031.6 | | 50% point = 034.3 | | 50% point = 016.2 | |

EXAMPLE 4

Photopolymerizable composition for the preparation of orthodontic appliances

An intimate or thorough mixture is prepared of:

41 g methacrylic acid ester mixture according to Example 2A
25.5 g polyglycol-400-dimethacrylate
17 g bishydroxymethyl-bicyclo [5.2.1.0$^{2,6}$] decanediacrylate
15.2 g polymer according to Example 2
0.3 g campherquinone
1 g methyldiethanol amine The readily spreadable composition is hardened by irradiating with light having a wavelength between 400 and 500 nm. A transparent molding practically free of lubricating layer is obtained by polymerization in vacuum with the photopolymerizer Visio-Beta of the ESPE company. Even after storage for long periods of time the composition remains practically unchanged.

Polymerizable layer thickness: 12 mm
Compressive strength: 412 MPa

EXAMPLE 5

Photopolymerizable dental material, combustible without leaving any residue, for the preparation of individual castings in dental technology (cf. DE-A 3,240,907).

54 g methacrylic acid ester mixture according to Example 2A
37 g diacrylate of ethoxylated bisphenol A
7.5 g polymer according to Example 3
0.2 g campherquinone
1.3 g triethanol amine 0.01 g Sudan Blue (BASF)
are worked to form a flowable mixture.

With this composition casting models can be made up in simple manner. Polymerization is effected by irradiating with light of a wavelength between 400 and 500 nm, for example with the polymerizers Visio-Alfa and Elipar of the ESPE company. The cast models obtained burn without leaving any residue. Even after relatively long storage time no viscosity change due to swelling and practically no segregation could be observed.

Polymerizable layer thickness: 8 mm
Compressive strength: 380 MPa

EXAMPLE 6

Photopolymerizable material for preparation and repair of plastic dental prosthesis.

64.7 g methacrylic acid ester mixture according to Example 2A
21.5 g bishydroxymethyl-bicyclo [5 2.1.0$^{2,6}$] decanediacrylate
12.5 g polymer according to Example 1
0.3 g campherquinone
1 g dimethylaminoethanol methacrylate
4 mg Sico fast red (BASF)

are worked to form a pasty composition.

On a plaster model this composition can be used to build up a dental prosthesis or to repair broken dentures. This composition is practically free from viscosity changes and segregation over longer periods of time.

The polymerization is carried out as in Example 4.
Polymerizable layer thickness: 6 mm
Compressive strength: 350 MPa

COMPARATIVE EXAMPLE

If in Example 6 instead of the precipitation polymer a commercially available bead polymer of fully crosslinked beads is used, with a comparable paste consistency the compressive strength obtained is only 65 MPa. Moreover, this filler sediments after only a few days.

EXAMPLE 7

Photopolymerizable dental material for making individual impression trays

A mixture is made from the following:
30.0 g bis-GMA
60.0 g triglycol dimethacrylate
10.0 g polymer according to Example 3
0.3 g campherquinone
1.0 g methyldiethanol amine A non-segregating composition is obtained which can be worked on a plaster model to give an individual impression tray.

The polymerization is carried out as described under Example 4.
Layer thickness: 8 mm
Compressive strength: 282 MPa

EXAMPLE 8

Photopolymerizing dental material, combustible without leaving any residue, for modelling purposes in dental technology.

A paste is made from:
30.00 g Bis-GMA
60.00 g triglycol dimethacrylate
8.50 g polymer according to Example 1
0.30 g campherquinone
1.00 g methyldiethanol amine
0.01 g Sudan Blue (BASF)

The modelling material obtained is free from any segregation and can be burnt without leaving any residue.

The use and polymerization are carried out as described under Example 5.
Layer thickness: 7 mm
Compressive strength: 253 MPa The present invention is, of course, in no way restricted to the specific disclosure of the specification and examples, but also encompasses any modifications within the scope of the appended claims.

What we claim is:

1. Polymerizable compositions in combination having a (meth)acrylic acid ester base and containing an insoluble organic filler, which is an organic non-swelling precipitation polymer combustible without leaving any residue as formed from at least one of the group consisting of acrylic acid esters and methacrylic acid esters and other copolymerizable monomers, and which provides precipitation polymers with 60 to 100 mol % of the (meth)acrylic acid esters being bi or polyfunctional,
said organic precipitation polymers having the following properties:
   (a) they consist of substantially irregular agglomerate or secondary particles having a grain size in a range of 0.2 to 200 μm,
   (b) the weight average of the grain size of said secondary particles is in a range of 5 to 100 μm,
   (c) said secondary particles are formed from primary particles having a grain size in a range of 0.05 to 2 μm, and
   (d) the BET surface area is in a range of 5 to 300 m$^2$/g.

2. Compositions in combination according to claim 1, in which the proportion of the precipitation polymers in the total composition is 2 to 60% by weight.

3. Compositions in combination according to claim 2, in which the proportion of the precipitation polymers in the total composition is 5 to 40% by weight.

4. Compositions in combination according to claim 3, in which the proportion of the precipitation polymers in the total composition is 5 to 25% by weight.

5. Compositions in combination according to claim 1, in which the precipitation polymers have the following properties:
   (e) the weight average of the grain size of said secondary particles is 10 to 50 μm,
   (f) the grain size of said primary particles is 0.1 to 1 μm, and
   (g) the BET surface area is 10 to 200 m$^2$/g.

6. Compositions in combination according to claim 5, in which the BET surface area is 50 to 100 m$^2$/g.

7. In a process for the preparation of compositions having a (meth)acrylic acid ester base and containing an insoluble organic filler which is an organic non-swelling precipitation polymer combustible without leaving any residue as formed from at least one of the group consisting of acrylic acid esters and methacrylic acid esters and other copolymerizable monomers, and which provides precipitation polymers with 60 to 100 mol % of the (meth)acrylic acid esters being bi or polyfunctional,
said organic precipitation polymers having the following properties:
   (a) they consist of substantially irregular agglomerate or secondary particles having a grain size in a range of 0.2 to 200 μm,
   (b) the weight average of the grain size of said secondary particles is in a range of 5 to 100 μm, (c) said secondary particles are formed from primary particles having a grain size in a range of 0.05 to 2 μm, and (d) the BET surface area is in a range of 5 to 300 m²/g, the improvement in combination therewith which includes the step of mixing together (meth-)acrylic acid esters, said precipitation polymers, and optionally one or more of the group consisting of initiators, stabilizers, inhibitors, coloring agents, pigments, opacifying agents, and X-ray contrast agents.

8. Polymerizable compositions specifically designated as dental compositions in combination having a (meth)acrylic acid ester base and containing an insoluble organic filler which is an organic non-swelling precipitation polymer combustible without leaving any residue as formed from at least one of the group consisting of acrylic acid esters and methacrylic acid esters and other copolymerizable monomers, and which provides precipitation polymers with 60 to 100 mol % of the (meth)acrylic acid esters being bi or polyfunctional, said organic precipitation polymers having the following properties:

(a) they consist of substantially irregular agglomerate or secondary particles having a grain size in a range of 0.2 to 200 μm, (b) the weight average of the grain size of said secondary particles is in a range of 5 to 100 μm, (c) said secondary particles are formed from primary particles having a grain size in a range of 0.05 to 2 μm, and (d) the BET surface area is in a range of 5 to 300 m²/g;

said organic precipitation polymers being provided as strengthening fillers in dental materials on the basis of mono, bi or polyfunctional (meth)acrylic acid esters, said fillers enabling monocomponent preparations to be made that exhibit neither swelling nor sedimentation behavior and even after storage for long periods of time, the composition remains unchanged and stable.

9. Polymerizable compositions specifically designated as dental compositions in combination having a (meth)acrylic acid ester base and containing an insoluble organic filler which is an organic non-swelling precipitation polymer combustible without leaving any residue as formed from at least one of the group consisting of acrylic acid esters and methacrylic acid esters and other copolymerizable monomers, and which provides precipitation polymers with 60 to 100 mol % of the (meth)acrylic acid esters being bi or polyfunctional, said organic precipitation polymers having precipitation polymer particles including the following properties:

(a) they consist of substantially irregular agglomerate or secondary particles having a grain size in a range of 0.2 to 200 μm, (b) the weight average of the grain size of said secondary (c) said secondary particles are formed from primary particles having a grain size in a range of 0.05 to 2 μm, and (d) the BET surface area is in a range 5 to 300 m²/g;

said organic precipitation polymers being provided as strengthening fillers in dental materials on the basis of mono, bi or polyfunctional (meth)acrylic acid esters, said fillers enabling monocomponent preparations to be made that exhibit neither swelling nor sedimentation behavior and even after storage for long periods of time the composition remains unchanged and stable;

said precipitation polymer particles accumulating together and not forming beads as in dispersion polymerization but rather forming porous agglomerates consisting of spherical primary and irregular secondary particles, said precipitation polymers being provided fully polymerized in amounts of 2 to 60% by weight, with respect to total composition; and said polymerizable composition for preparation of orthodontic appliances being readily spreadable and hardened by irradiating with light and having a wavelength in a range between 400 and 500 μm as well as being applicable to build up a dental prosthesis and to repair broken dentures with said composition being practically free from viscosity changes and segregation over longer periods of time.

10. Compositions according to claim 9, in which said polymers have a surface area in a range between 10 and 200 m²/g.

11. Compositions according to claim 10, in which said precipitation polymers are provided fully polymerized in amounts of 5 to 40% by weight with respect to total composition.

12. Compositions according to claim 9, in which said polymers have a surface area in a range between 50 and 100 m²/g.

13. Compositions according to claim 1, in which said precipitation polymers are provided fully polymerized in amounts of 5 to 40% by weight with respect to total composition.

14. Compositions according to claim 9, in which said precipitation polymers are provided fully polymerized in amounts of 5 to 40% by weight with respect to total composition.

* * * * *